United States Patent [19]

Smith

[11] Patent Number: 4,746,610

[45] Date of Patent: May 24, 1988

[54] EFFICIENT USE OF THERMAL ENERGY FROM AN INTERNAL COMBUSTION ENGINE IN ETHANOL PRODUCTION

[75] Inventor: R. Wayne Smith, Warsaw, Ind.

[73] Assignees: Douglas W. Wills, Indianapolis, Ind.; Linda Wills Maher, Corrales, N. Mex.; Nancy Wills Coffin, Auburn, Ind.; a part interest to each

[21] Appl. No.: 463,123

[22] Filed: Feb. 2, 1983

[51] Int. Cl.⁴ .......................... C12P 7/06; B01D 3/00
[52] U.S. Cl. .................................... 435/161; 435/316; 203/19; 203/21; 203/22; 203/25; 203/27
[58] Field of Search ............... 435/161, 155, 156, 157, 435/287, 316; 123/1 A; 426/807; 203/22, 23, 21, 19, 18

[56] References Cited

U.S. PATENT DOCUMENTS

| | | | |
|---|---|---|---|
| 2,389,789 | 11/1945 | Latham | 203/21 |
| 4,325,329 | 4/1982 | Taylor | 123/3 |
| 4,327,184 | 4/1982 | Johnson et al. | 435/287 |
| 4,340,446 | 7/1982 | Crawford | 203/19 |
| 4,344,828 | 8/1982 | Melton | 203/19 |
| 4,345,972 | 8/1982 | Hannebaum et al. | 203/19 |
| 4,371,623 | 2/1983 | Taylor | 435/316 |
| 4,400,469 | 8/1983 | Harris | 435/161 |

Primary Examiner—Sam Rosen
Assistant Examiner—William J. Herald
Attorney, Agent, or Firm—Wendell E. Miller

[57] ABSTRACT

An ethanol-producing plant and a method is provided for producing ethanol from sugars, starches, or cellulose. Some ethanol-producing plants consume more thermal energy than they produce. The present invention solves the efficiency problem by utilizing an internal combustion engine with high-efficiency mechanical drives for providing the mechanical power requirements of the ethanol-producing plant and by utilizing the thermal energy of engine coolant and exhaust to provide some, or all, of the thermal energy requirements of the ethanol-producing plant. The method includes electrically loading the internal combustion engine to increase the thermal losses of the engine to equal the thermal energy requirements of the steps of the ethanol-producing process.

39 Claims, 2 Drawing Sheets

EFFICIENT USE OF THERMAL ENERGY FROM AN INTERNAL COMBUSTION ENGINE IN ETHANOL PRODUCTION

The present invention relates generally to an energy efficient method for producing alcohol. More particularly, the present invention relates to a method for alcohol in which heat losses of an internal combustion engine, including heat losses of engine coolant and of engine exhaust, are used for thermal energy requirements of the process.

Even more particularly, the present invention relates to a method for producing ethanol from tubers of artichokes, and use of the thermal energy of an internal combustion engine, including the thermal energy of the engine coolant and the engine exhaust, for thermal energy requirements of the process.

Further, the present invention includes selectively adjusting the mechanical load on the internal combustion engine to provide thermal energy that is sufficient to supplement other thermal energy for one, or any, or all of the steps of the process that require thermal energy, or to provide thermal energy that is sufficient for one, or any or all of the steps of the process without any thermal energy being supplied by another source.

BACKGROUND ART

Processes for producing ethanol, or ethyl alcohol, from materials that contain sugar, from materials that contain starch, and from materials that contain cellulose.

Production of ethanol from materials that contain simple sugars is the easiest; because simple sugars can be fermented by the addition of yeast.

Production of ethanol from materials that contain starches is more difficult and costly; because the starches must be converted to simple sugars before the yeast can ferment the material and produce ethanol.

The breaking down of starches into sugars includes mechanically reducing the starchy material to the smallest practical size by milling or grinding, making a slurry of the starchy material and water, and heating the slurry with a first enzyme to a temperature that is high enough to break the cell walls of the starch. This step is called enzymatic hydrolysis and it produces dextrins from the starches.

The dextrins are then reduced to simple sugars, or glucose, by the use of a second enzyme. This second step is called saccharification.

Breaking down cellulose into material that is fermentable is difficult and costly. Commonly this process includes the use of acid and heat; and the process is called acid hydrolysis.

Materials containing sugar, which are suitable for the production of ethanol, include: sugar cane, sugar beets, sweet sorghum, American artichokes, fodder bets, and fruit crops such as grapes, apricots, peaches, and pears.

Materials containing starch, which are suitable for the production of ethanol, include grains such as corn, barley, wheat, and sorghum, and tubers such as potatoes and sweet potatoes.

Materials that contain cellulose include stalks and leaves of sugar and starch crops, and forage crops. Forage crops, such as forage sorghum and Sudan grass, in early stages of growth, include a larger proportion of their carbohydrates in starch and a smaller proportion of their carbohydrates in cellulose. In addition there is very little lignin in these two forage crops in the early stages of growth; so conversion to sugars is more efficient.

The conversion of starch to glucose normally requires that the temperature of the slurry be raised to ninety-three degrees Celcius (two hundred degrees Farenheit) and that the slurry be held at this temperature for two and one-half hours. Then for the saccharification step, the temperature must be dropped to between sixty degrees and fifty degrees Celcius (between one hundred forty and one hundred twenty-two degrees Farenheit).

The heating, temperature maintaining, and temperature reducing steps that are required to convert starch to sugar adds to the energy requirements of the distillation process; so that, in some cases, the production of ethanol requires more energy, in coal and electricity, than the energy of the ethanol that is produced.

DISCLOSURE OF THE INVENTION

In accordance with the broader aspects of the present invention, there is provided a method for the production of ethanol from a fermentable material, and for the improvement of the overall efficiency of the thermodynamic cycle by utilizing the thermal losses of an internal combustion engine to provide part or all of the thermal energy needs of one or more of the process steps.

Preferably, the thermal energy of the internal combustion engine that is used includes the thermal energy that is added to engine coolant as the coolant flows through the engine; and the thermal energy that is used in the preferred process includes the thermal energy of the exhaust gases of the engine.

Preferably, this use of the thermal energy of exhaust gases includes the increasing of the thermal energy of the engine coolant by the use of a gas-to-fluid heat exchanger.

Further, preferably, the heat of condensation of the exhaust gases is recovered by lowering the temperature of the exhaust gases below the temperature of condensation of water vapor. Thus, the heat content of the water vapor, that is one of the products of combustion, is salvaged.

Further, in a preferred process, the fuel for the internal combustion engine is hydrous ethanol that contains at least five percent water. The use of hydrous ethanol for engine fuel obviates the cost of adding a drying step to the distillation process.

Also, the reducing of exhaust gases below the temperature of condensation in the heat exchanger reclaims the thermal energy that was used in vaporizing the portion of the fuel that was water.

Thus, in the present invention, the thermal efficiency of an ethanol-producing plant is improved by utilizing heat losses of an internal combustion engine to provide all of the thermal energy that is required for one or more of the steps of the process, or to supplement another source of thermal energy for one or more of the steps of the process.

In the preferred process, the mechanical output of the internal combustion engine is used to provide power for the various process steps. This mechanical output of the engine is connected to each apparatus by a chain drive, by a belt drive, by a gear drive, or by direct connection to high power transmission efficiencies are achieved.

The mechanical output of the engine is used to pump coolant for the transmission of thermal energy, to reduce the size of the stock material, to press a fermentable liquid from a fermentable material, to pump water for the condensor, and to rotate the drum of the residue dryer.

Further, the mechanical output of the engine may be used to power a compressor or a generator. The compressor may be used to compress the carbon dioxide gas that is a byproduct of the fermentation process; or the compressor may be used as a part of a refrigeration unit for air conditioning or cold storage.

The generator is used as a variable load for the mechanical output of the internal combustion engine. The load of the generator is adjusted to supplement all other mechanical loads on the engine, and to achieve a load on the engine that provides the required quantity of thermal energy.

That is, the total mechanial load on the engine, including the variable load of the generator, is adjusted to provide thermal energy, including both coolant and exhaust thermal energy, that is sufficient, as a supplementary source of thermal energy, or as a sole source of thermal energy, for one or more steps of the process.

The electrical power that is produced by the generator may be used to charge batteries and thereby to supply a source of electricity for the process, or for the home or farm where the ethanol plant is located; or the electrical power of the generator may be sold to the utility company that supplies electrical power to the ethanol plant, thereby reducing the total electrical power that is purchased.

A fermentable material for ethanol production should contain between ten and twenty percent of sugar by weight. If the content of sugar is too low, the yeast may die; and if the content of sugar is high, the yeast will run wild in reproducing itself rather than producing enzymes.

In the present invention, the preferred process utilizes tubers of the American artichoke as the fermentable material. The percentage of sugar in the American artichoke is almost in the middle of the acceptable range at fifteen and nine-tenths percent.

It is common practice in the art to make a dry feed stock for animals from the residue of the fermentation process. Since neither enzymatic hydrolysis, nor saccharification, nor the fermentation process changes the protein content of the material, the dried residue is a nutritious feed stock.

In the present invention, in a preferred method the fermentable liquid is separated from the stock material prior to fermentation. However, whether the process includes fermentation of the stock material, or whether the process includes separation of the fermentable material from the stock material before fermentation, the present invention includes the use of thermal losses of an internal combustion engine as a source of thermal energy for producing an anhydrous feed stock.

BEST MODE FOR CARRYING OUT THE INVENTION

Figure 1:
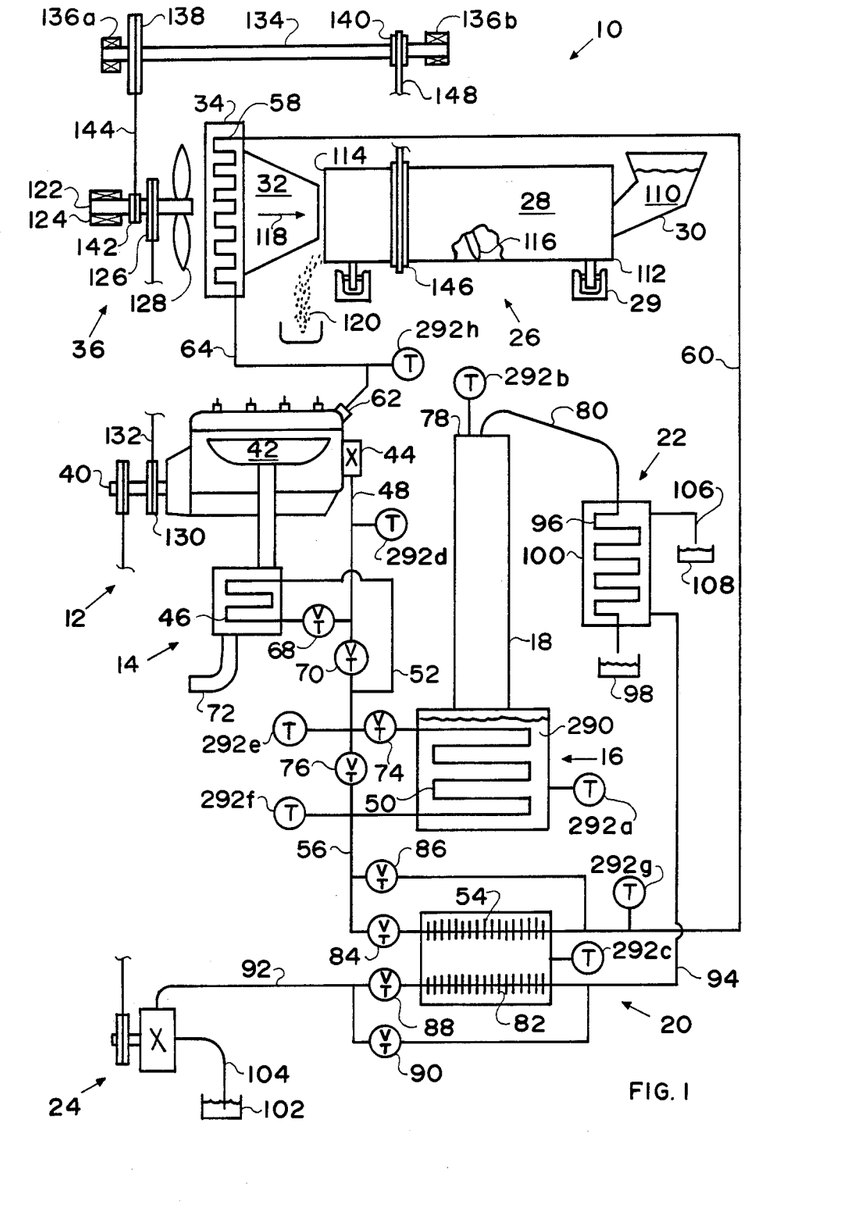
FIG. 1 is a schematic drawing of an ethanol-producing plant that includes apparatus for fermentation, distillation, condensation, and drying, together with an internal combustion engine, a heat transfer system that utilizes engine coolant, and a heat exchanger for increasing the thermal energy of the engine coolant by reclaiming the thermal energy of the exhaust gases.

Referring now to the drawings, and more particularly to FIG. 1, an ethanol-producing plant 10 includes an internal combustion engine 12, a heat exchanger 14, a still 16 having a redistillation tower 18, a vat or fermentation room 20, a condenser 22, a water pump 24, and a dryer 26.

The dryer 26 includes a dryer drum 28 that is cylindrical in shape, that is substantially horizontally disposed and that is supported by roller assemblies 29, a hopper 30, a duct 32, a heat exchanger 34, and a fan assembly 36.

The internal combustion engine 12 includes a crankshaft 40, an exhaust manifold 42, and a coolant pump 44.

The fuel that is burned by the engine 12 produces mechanical power at the crankshaft 40, and produces losses that are in the form of thermal energy. This thermal energy leaves the engine 12 in the form of convection losses, in the form of increased thermal energy of the engine coolant as it flows through the engine 12, and in the form of hot exhaust gases.

Fluid or liquid coolant flowing from the coolant pump 44 flows to a heat exchanger element 46 in the heat exchanger 14 via a conduit 48, from the heat exchanger element 46 to a heating coil 50 in the still 16 via a conduit 52, from the heating coil 50 to a heat exchanger element 54 in the vat or fermentation room 20 via a conduit 56, and from the heat exchanger element 54 to a heat exchanger element 58 of the heat exchanger 34 via a conduit 60. From the heat exchanger element 58, the coolant flows to a return port 62 of the engine 12 via a conduit 64.

Discussing now the flow of coolant and thermal energy in more detail, the coolant that enters the return port 62 flows through the internal combustion engine 12, receives thermal energy from cooling passages (not shown) of a water jacket (not shown) of the engine 12, and is discharged from the engine 12 by the coolant pump 44.

The coolant that is pumped into the conduit 48 by the coolant pump 44 receives additional thermal energy from the exhaust gases as the exhaust gases flow through the heat exchanger element 46 of the heat exchanger 14.

The quantity of thermal energy that is added to the coolant in the heat exchanger 14 is controlled by selective adjustment of valves 68 and 70.

Valves 68 and 70 are adjusted to control fluid flow through the heat exchanger element 46 by bypassing any desired portion of the fluid flow from the conduit 48 to the conduit 52 through the valve 70.

The valves 68 and 70 are selectively adjusted to lower the temperature of the exhaust from the exhaust manifold 42 to below the heat of condensation of the water vapor in the exhaust gases, thereby reclaiming the heat of condensation of the thermal energy in the exhaust gases flowing through the heat exchanger element 46.

Preferably, the heat exchanger 14 is sized to raise the temperature of the coolant flowing through the heat exchanger element 46 to within one degree Celcius (two degrees Farenheit) of the temperature of the exhaust gases which are discharged from an exhaust pipe 72.

Coolant discharged from the heat exchanger element 46 is directed to the heating coil 50 of the still 16, and/or is selectively bypassed to the conduit 56 by selective adjustment of valves 74 and 76.

The valves 74 and 76 are adjusted to maintain the temperature of the fluid in the still 16 to somewhat above the boiling point of ethanol which is 78 degrees Celcius (172 degrees Farenheit).

The still 16 must be maintained at a temperature that is above the boiling point of ethanol, but it must also be maintained at a boiling point lower than the boiling point of water.

Further, for the functioning of the redistillation tower 18, the temperature from the still 16 to a top 78 of the redistillation tower 18 must progressively decrease; and the temperature at the top of the distillation tower 78 must be maintained at the boiling point of ethanol.

As ethanol is distilled from water by the still 16, because of an increase in the vapor pressure of the water in the still at an elevated temperature, some water vapor is condensed in the redistillation tower 18. The condensed water flows back down the redistillation tower 78 into the still 16; and so the ethanol vapor that proceeds outwardly into a conduit 80 is of a higher proof because of the redistillation tower 18.

Coolant leaving the heating coil 50 of the still 16 flow through the conduit 56 to valves 84 and 86. Valves 84 and 86 are selectively adjusted to provide flow of coolant through the heat exchanger element 54 of the vat or fermentation room 20 and/or to bypass some or all of the coolant flow around the heat exchanger element 54 to the conduit 60, depending upon whether or not control of the temperature of the vat or fermentation room 20 requires the addition of thermal energy.

It is possible to control the temperature of fluid in a distaillation vat either by controlling the temperature of the room wherein the vat is located, or by controlling the temperature of the fluid in the vat itself. Therefore, in the illustration of FIG. 1, the number 20 is used to designated either a vat or the fermentation room in which a fermentation vat is located.

Temperature of the vat or fermentation room 20 is controlled by adding thermal energy by coolant flow through the heat exchanger element 54 or by extracting thermal energy by flow of well water through a heat exchanger element 82 of the vat or fermentation room 20.

Flow of well water from the water pump 24 is supplied to valves 88 and 90 via a conduit 92; and the well water is directed through the heat exchanger element 82 and/or bypassed around the heat exchanger element 82 to a conduit 94 by selective adjustment of the valves 88 and 90.

Returning now to a discussion of the flow of coolant, coolant is supplied to the heat exchanger element 58 of the heat exchanger 34 by the conduit 60; and the heat exchanger element 58 extracts thermal energy from the coolant for use by the dryer 26.

The coolant then flows from the heat exchanger element 58 to the return port 62 of the engine 12 via the conduit 64.

Returning again to a discussion of the ethanol vapor in the conduit 80, the ethanol vapor in the conduit 80 flows into a condensor coil 96 of the condensor 22, the ethanol vapor is condensed, and ethanol flows out of the condensor coil 96 into a container 98. Preferably, the ethanol that is collected in the container 98 has a proof of at least 160.

The condensor 22 includes a shell 100 that encases the condensor coil 96; and well water from the conduit 94 flows into the condenser shell 100 via the heat exchanger element 82 and/or the valve 90, cooling the condensor coil 96. This well water, which had been drawn from a well 102 and a conduit 104 by the water pump 24, is returned to the ground via a conduit 106 and a disposal well 108 as it flows from the condensor shell 100.

Considering now the operation of the dryer 26 of FIG. 1, wet bulk residue 110, that is a fermented residue, or that is an unfermented residue from which a fermentable liquid has been removed, is placed into the hopper 30.

The wet bulk residue 110 is fed into an end 112 of the dryer drum 28 by the hopper 30. The wet bulk residue 110 is augered toward an end 114 of the dryer drum 28 by rotation of the dryer drum 28, and by an auger 116 that is helically disposed inside the dryer drum 28.

As the wet bulk residue 110 is moved from the end 112 toward the end 114 of the dryer drum 28, the fan assembly 36 blows air 118 through the heat exchanger 34, into the end 114 of the dryer drum 28, and through the dryer drum 28. The air 118 picks up thermal energy in the heat exchanger 34; and the heated air dries the wet bulk residue 110 into an anhydrous bypoduct 120 which is discharged from the end 114.

Considering now the mechanical power transmission portion of the present invention, mechanical power from the engine 12 is transmitted by direct connection to the crankshaft 40, by means of a sprocket and chain drive, or by means of a pulley and belt drive. In the description which follows, sprocket and chain drives are considered to be interchangeable with pulley and belt drives; however, for simplicity of description, alternate names, that is, pulley or sprocket, and belt or chain, are not used.

Referring again to FIG. 1, the fan assembly 36 includes a jackshaft 122 that is journaled in a bearing 124, a sprocket 126 that is secured to the jackshaft 122, and fan blades 128 that are secured to the jackshaft 122.

The jackshaft 122 and the fan blades 128 are rotated by a sprocket 130 that is attached to the crankshaft 40, and a chain 132 that transmits power from the sprocket 130 to the sprocket 126.

The dryer drum 28 is rotated by the engine 12 by mechanical power that flows from the crankshaft 40 to the jackshaft 122, from the jackshaft 122 to a jackshaft 134, and from the jackshaft 134 to the dryer drum 28.

The jackshaft 134 is journaled in bearings 136a and 136b. The jackshaft 134 carries a sprocket 138, and a sprocket 140. The sprocket 138 receives mechanical power from the jackshaft 122 by means of a sprocket 142 that is mounted on the jackshaft 122, and by a chain 144 that interconnects the sprockets 142 and 138.

The jackshaft 134 delivers mechanical power to the dryer drum 28 by means of a sprocket 146 that is disposed circumferentially around the dryer drum 28, and a chain 148 that engages the sprockets 140 and 146.

Figure 2:
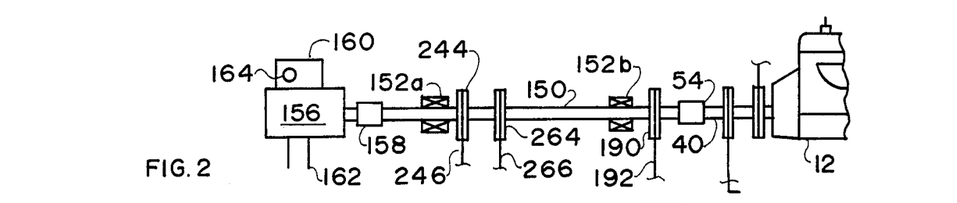
FIG. 2 is a schematic drawing showing the portion of the ethanol-producing plant that includes the mechanical output of the internal combustion engine, a jackshaft that is coupled to the crankshaft of the engine, a plurality of sprockets that are mounted to the jackshaft, and a generator that is coupled to the jackshaft.

Referring now to FIG. 2, a jackshaft 150 is journaled in bearings 152a and 152b and is coupled to the crankshaft 40 of the engine 12 by a coupling 154.

A direct current generator 156 is coupled to the jackshaft 150 by a coupling 158. The generator 156 includes a control 160; and the voltage output of the generator 156 at output terminals 162 is selectively adjusted by a knob 164 of the control 160.

The generator 156 serves as a part of the means for selectively loading the mechanical output of the internal combustion engine 12; and the purpose for selectively loading the output of the engine 12 is to increase the thermal energy of the engine 12, so that the thermal energy of the engine 12 is sufficient for part, or all, of the thermal energy requirements for one, or any, or all, of the processes of the ethanol-producing plant 10.

Figures 3, 4, 5, 6:
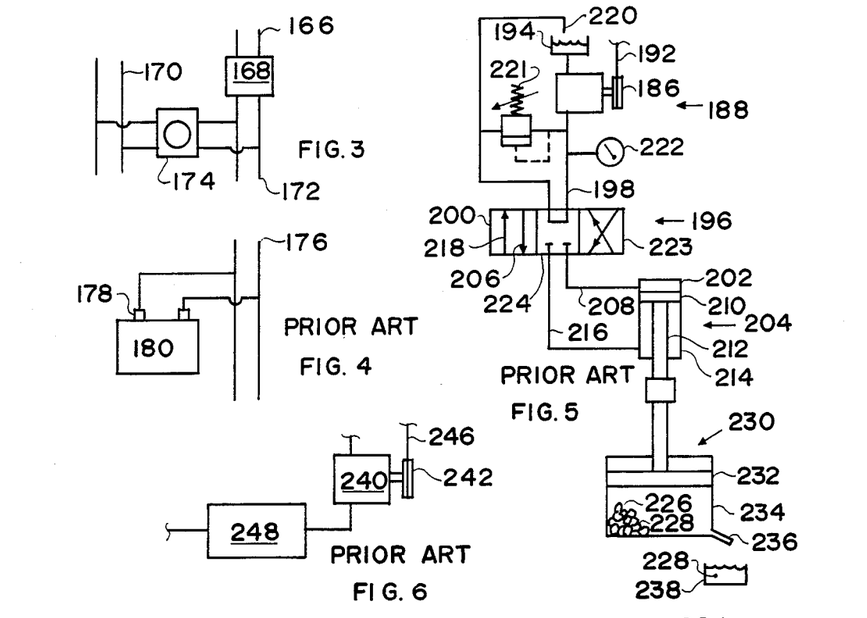
FIG. 3 is a schematic drawing showing the portion of the ethanol-producing plant that provides apparatus for converting direct current electrical power to alternating current electrical power, and for selling alternating current electrical power to a utility company.
FIG. 4 is a schematic drawing showing a portion of the ethanol-producing plant that provides apparatus for storing surplus electrical power that is produced by the generator of FIG. 2.
FIG. 5 is a schematic drawing of the portion of the ethanol-producing plant that provides hydraulic power, and that utilizes hydraulic power for the separation of a mixture of fermentable material and water from artichoke tubers.
FIG. 6 is a schematic drawing showing a compressor and pressure tank which may be used in conjunction with, or as a part of, the ethanol-producing for compressing and storing the carbon dioxide that is a byproduct of the fermentation process, or for powering a refrigeration unit compressor of an air conditioning system or cold storage plant.

The means for selectively loading the mechanical output of the engine 12 includes, in addition to the generator 156, either the apparatus of FIG. 3 or the apparatus of FIG. 4.

Referring now to FIGS. 2 and 3, the output terminals 162 of the generator 156 may be connected to respective ones of input terminals 166 of an inverter or converter 168 of FIG. 3. Direct-current electrical power applied to the input terminals 166 is converted into alternating current power that is of the same frequency as, and that is in phase with, alternating current electrical power in utility company power lines 170.

Referring now to FIG. 3, alternating current electrical power is available at service terminals 172; and this electrical power may be used for any purpose connected with the operation of the ethanol-producing plant 10, for exterior lighting, or for use around a farm or farmhouse.

The electrical power at the terminals 172 is furnished either by the generator 156 and the converter 168, or by the utility company power lines 170, depending upon whether or not one or more of the processes of the ethanol-producing plant 10 requires the loading of the generator 156 to produce additional thermal energy.

If the generator 156 and the converter 168 produce less electrical power than is required at the terminals 172, then the additional electrical power is supplied to the terminals 172 from the utility company power lines 170, and a watt-hour meter 174 accumulates charges against the user.

However, if the generator 156 and the converter 168 produce more electrical power than is required at the terminals 172, then the surplus electrical power is delivered to the utility company power lines 170 through the watt-hour meter 174, and the watt-hour meter 174 substracts the power that is delivered to the power lines 170 from the electrical power that is delivered from the power lines 170 to the terminals 172.

Referring now to FIGS. 2 and 4, terminals 176 of the apparatus and circuitry of FIG. 4 are connected to respective ones of battery terminals 178 of a battery 180. Then connection of the terminals 176 of FIG. 4 to the terminals 162 of FIG. 2 provides a means for storing electrical power; and the means for selectively loading the engine 12 becomes the generator 156 and the battery 180.

Electrical power at terminals 182 may be supplied directly from the generator 156 of FIG. 2, or may be supplied from the battery 180, depending upon the demand at the terminals 182 in comparison with the output of the generator 156 that is needed to increase the thermal energy of the engine 12 for use in meeting thermal energy requirements of the ethanol-producing plant 10.

Referring now to FIGS. 2 and 5, and more particularly to FIG. 5, a sprocket 186 is attached to a hydraulic pump 188. The hydraulic pump 188 is driven from the crankshaft 40 of the engine 12 by means of a sprocket 190 that is attached to the jackshaft 150, and a chain 192 that transmits mechanical power from the sprocket 190 to the sprocket 186.

The hydraulic pump 188 receives hydraulic fluid from a reservoir 194 and delivers hydraulic fluid to a control valve 196 via a conduit 198.

When the control valve 196 is in a position 200, fluid is delivered from the hydraulic pump 188 to an end 202 of a hydraulic cylinder 204 via a flow path 206 in the control valve 196, and via a conduit 208, forcing a piston 210 and a piston rod 212 downwardly.

When the control valve 196 is in the position 200, fluid from an end 214 of the cylinder 204 is returned to the reservoir 194 via a conduit 216, a flow path 218 in the control valve 196, and a conduit 220.

A pressure relief valve 221, of the type whose opening pressure is manually adjustable, is connected between the conduit 198 and the conduit 220. The relief valve 221 adjustably limits the maximum pressure of the pump 188 and the downward force of the platen 232. A pressure gauge 222 is provided for reference in manually adjusting the relief valve 221.

The operation of the hydraulic circuitry of FIG. 5 is conventional; therefore, it is not necessary to describe the functioning of the circuit when the control valve 196 is moved to a position 223 or to a neutral position 224.

When a macerated material 226 that contains a fermentable mixture 228 of a fermentable material and water is placed into a press 230, downward movement of the piston rod 212 forces a platen 232 of the press 230 downwardly into a tub 234 of the press 230, pressing the fermentable mixture 228 of fermentable material and water out of the macerated material 226. The fermentable mixture 228 of fermentable material and water is discharged from the tub 234 through a spout 236 and into a container 238.

Referring now to FIGS. 2 and 6, the mechanical power requirements on the engine 12 may be increased by operating a gas compressor 240 from the engine 12. A sprocket 242 is attached to the gas compressor 240, a sprocket 244 is attached to the jackshaft 150 of FIG. 2, and a chain 246 delivers power from sprocket 244 to the sprocket 242.

The gas compressor 240 may be used to compress carbon dioxide that is produced as a byproduct of fermentation in the vat or fermentation room 20, and the compressed gas may be stored in a pressure tank 248; or the gas compressor 240 may be used to operate a refrigeration compressor for a mechanical air conditioning unit or for a cold storage unit.

Figures 7, 8:
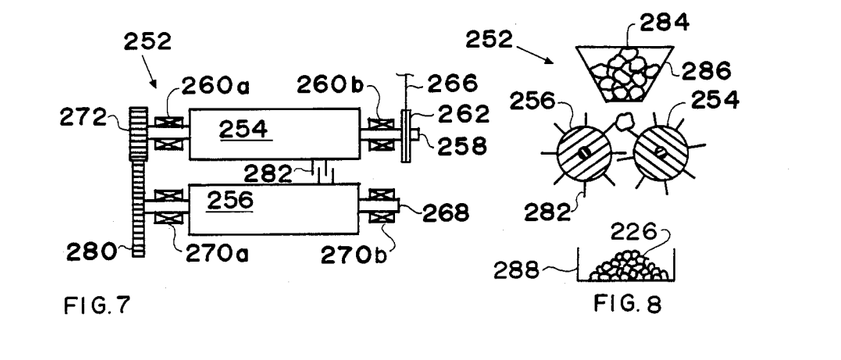
FIG. 7 is a top view showing the portion of the ethanol-producing plant that is used for macerating tubers or other stock material.
FIG. 8 is an end view of the apparatus of FIG. 7.

Referring now to FIGS. 2, 7 and 8, and more particularly to FIGS. 7 and 8, a macerator 252 includes macerator rolls 254 and 256.

The macerator roll 254 includes a shaft 258; and the shaft 258 is journaled in bearings 260a and 260b. The macerator roll 254 is driven by a sprocket 262 that is attached to the shaft 258, a sprocket 264 that is attached to the jackshaft 150 or FIG. 2, and a chain 266 that connects the sprocket 264 to the sprocket 262.

The macerator roll 256 includes a shaft 268; and the shaft 268 is journaled in bearings 270a and 270b. The macerator roll 256 is driven by a gear 272 that is attached to the shaft 258, and a gear 280 that is attached to the shaft 268 and that meshes with the gear 272.

The gears 272 and 280 are designed to produce a speed of rotation of the roll 256 that is half of the speed of rotation of the roll 254; and the direction of rotation of the rolls 254 and 256 is opposite.

The macerator rolls 254 and 256 include macerator teeth 282. The teeth 282 are disposed circumferentially around each of the rolls 254 and 256, and project radially outward therefrom. The teeth 282 also are spaced longitudinally along the rolls 254 and 256, with the teeth 282 of the roll 254 being longitudinally spaced intermediate the teeth 282 of the roll 256.

The teeth 282 of both of the rolls, 254 and 256, move downwardly intermediate of the rolls 254 and 256 as viewed in FIG. 8, the teeth 282 of the roll 254 moving more rapidly and passing down between respective rows of teeth 282 of the roll 256, tearing, or macerating, material 284 that is fed between the rolls 254 and 256 by a hopper 286.

The macerated material 226 is collected in a container 288.

Referring again to FIG. 1, a thermometer 292a is provided for monitoring temperature in the still 16, a thermometer 292b is provided for monitoring temperature at the top 78 of the redistillation tower 18, a thermometer 292c is provided for monitoring temperature in the vat or fermentation room 20, and thermometers 292d-292h are provided for monitoring the supplying of thermal energy from the engine coolant, and for determining the adjustment of the various valves that control the flow of the engine coolant.

Considering now the steps of the method of the present invention, in a preferred process, tubers which are known as American artichokes, as used as the material 284.

The steps of the method include: feeding the material 284 into the hopper 286 of FIG. 8, macerating the tubers or material 284 into macerated material 226 by passing the material 284 between the rolls 254 and 256 and tearing or macerating the material 284 by action of the teeth 282, placing the macerated material 226 into the press 230 of FIG. 4, and pressing, a fermentable mixture 228 of fermentable material and water out of the macerated material 226 so that the fermentable mixture 228 is separated from the wet bulk residue 110 of FIG. 1.

The steps of the method further include: placing the fermentable mixture 228 into the vat 20, controlling the temperature of the fermentable mixture 228 by supplying thermal energy to the fermentable mixture 228 or to the vat or fermentation room 20, or by removing thermal energy from the fermentable mixture 228, or from the vat or fermentation room 20, and holding the temperature of the fermentable mixture 228 at a temperature of approximately 30 degrees Celcius (86 degrees Farenheit) until the fermentable mixture 228 is changed to a fermented mixture 290 of ethanol and water.

The steps of the method further include: placing the fermented mixture 290 of ethanol and water into the still 16, supplying thermal energy to the still 16 to bring the mixture 290 of fermentable material up to a temperature that is greater than the boiling point of ethanol and that is lower than the boiling point of water, maintaining the temperature in the still 16 while distilling the ethanol from the water, maintaining the temperature at the top of the redistillation tower at, or slightly above, the boiling point of ethanol, passing the ethanol vapor through the condensor 22, removing thermal energy from the heat exchanber element 96 by pumping well water, or water from some other external source, through the shell 100 of the condensor 22, and collecting distilled ethanol in the container 98.

The steps of the method also include: placing the pulp, or wet bulk residue 110, into the dryer 26, rotating the dryer drum 28, applying heat, or thermal energy, to the dryer 26 and to the wet bulk residue 110, and producing an anhydrous byproduct 120 that has nutritional value.

Further, the steps of the method include: providing an internal combustion engineer 12 of the type that adds thermal energy to a coolant as the coolant flows through the engine, adjusting the load of the mechanical output of the engine to provide thermal energy that is sufficient to supplement one, or any, or all of the thermal energy requirements of the steps of the method, or to provide thermal energy that is sufficient for one, or any, or all of the thermal energy requirements.

The loads that are placed upon the engine 12, which have been illustrated, comprise utilizing the engine for the following steps: macerating tubers, powering a hydraulic pump for pressing a fermentable mixture 228 out of the macerated tubers 226, rotating the dryer drum 28, pumping water, compressing gas, and powering a generator.

The mechanical output of the engine is used for seaprating a fermentable mixture 228 of a fermentable material and water from a pulp or wet bulk residue 110 by the macerating step and the pressing step.

The step of adjusting the mechanical load of the engine 12 is in addition to whatever loads are placed upon the engine 12 by the various steps of the method, and/or any other loads that may be placed upon the engine 12, either intermittently, or constantly.

The step of adjusting the mechanical load of the engine 12 includes connecting the electrical output of the generator 156 to a watt-hour meter 174, and connecting the watt-hour meter 174 to utility company power lines 170; or the step of adjusting the mechanical load includes connecting the electrical output of the generator 156 to a battery 180. Thus, in the broader sense, the step of adjusting the mechanical load of the engine includes electrically loading.

The steps of the method include utilizing thermal energy of the coolant for supplying thermal energy for the various steps, increasing the thermal energy of the coolant by reducing the temperature of the exhaust gases, and utilizing the heat of condensation of water vapor in the exhaust gases by cooling the exhaust gases below the condensation temperature of water vapor.

Thermal energy of the coolant is used for the controlling step of the fermentation process, for the supplying step of the distilling process, and for the applying step of the drying process.

The steps of the process include condensing ethanol vapor into ethanol by removing thermal energy from the ethanol vapor, or from the condensation coil 96, and controlling the temperature of the fermentable mixture 228 and/or the temperature of the vat or fermentation room 20 by removing thermal energy. These two removing steps include pumping water.

In summary, the method of the present invention is adaptable for producing ethanol from materials that contain sugars, starches, and/or cellulose. However, if materials other than simple sugars are used, steps must be added to the steps of the present invention to convert the material to fermentable simple sugars before utilizing the steps of the present invention.

Thus, the step of providing a fermentable mixture may include the macerating and pressing steps, or this providing step may include the conversion of starches and/or cellulose to simple sugars.

Further, the providing step does not necessarily require the removal of the fermentable material from the pulp. That is, artichoke tubers, or similar material, may be crushed, mixed with water to make a slurry, and fermented before removing the pulp or wet bulk residue.

Methods for producing ethanol from materials containing sugars, starches, and/or cellulose materials are well known and can be found in such references as FUEL FROM FARMS—A GUIDE TO SMALL SCALE ETHANOL PRODUCTION. This book can be obtained from the Superintendent of Documents of the U.S. Government Printing Office. Therefore, there is no necessity of repeating all prior art information along with the steps of the present invention.

In summary, the improvement in method of the present invention includes a method for the processing of fermentable material prior to fermentation, and to a method for drying a wet bulk residue into an anhydrous byproduct.

However, the most important improvement of the invention resides in the use of thermal energy losses of an internal combustion engine 12 to supplement another source of thermal energy in the supplying of thermal energy for one, or several, or all, of the steps in an ethanol-producing plant that require thermal energy, or to supply all of the thermal energy for one, or several, or all of the steps.

An important improvement of the present invention is that the method of the present invention includes selective adjustment of mechanical loads on the output of the internal combustion engine to meet the thermal energy requirements of the process.

The selective loading of the engine includes electrically loading the engine to provide thermal energy that is sufficient to supplement, or to provide the total thermal energy requirements of, one or more of the process steps in the production of ethanol.

More specifically, the method includes the use of an internal combustion engine of the type that adds thermal energy to a coolant as the liquid coolant passes through the engine, and the addition of thermal energy to this coolant from the thermal energy of exhaust gases of the engine.

The thermal energy of the internal combustion engine that is used includes the thermal energy that is added to coolant as the coolant flows through the engine, the thermal energy of the exhaust gases, and the thermal energy of the heat of condensation of water vapor in the exhaust gases.

The energy efficiency of the process is improved by the utilization of heat losses of an internal combustion engine to supplement, or as the sole source for, the energy requirements of one, or more, or all processes of the distillation plant.

In addition, the overall operating efficiency of the ethanol plant is improved by utilizing highly efficient mechanical drives to connect the mechanical output of the internal combustion engine to the various components which require mechanical power.

Further, the overall efficiency of the process is enhanced by producing electrical power whenever the various mechanical loads on the engine do not produce sufficient thermal energy for the steps of the process. The electrical power that is produced may be stored in a storage battery, or the electrical power may be converted to alternating current power and sold to the utility company.

Preferably, the internal combustion engine is fueled with ethanol which is produced by the ethanol-producing plant 10; and preferably, this fuel has a proof of at least 160, and not more than 190.

It is well known that internal combustion engines of the type using carburetion can be adapted to run on ethanol that includes as much as twenty percent water.

The use of hydrous ethanol as a fuel eliminates the cost of removing the last five percent of water from ethanol by an expensive drying process, thereby further improving the overall efficiency and cost effectiveness of the present invention.

The present invention contemplates the use of the stalks of the American artichokes as a source of thermal energy, either in the form of bundles, or as a chopped material. This stalk material may be used as a source of thermal energy for the ethanol-producing plant, as a source of thermal energy for a farmhouse, or as a saleable product.

While particular apparatus and a particular method have been described, it should be understood that the scope of the present invention is to be limited only by the scope of the claims.

INDUSTRIAL APPLICABILITY

The invention provides an energy efficient distillation process which may be used by farm owners, by cooperatives for distillation operations, or by medium-size companies that wish to produce ethanol from a fermentable material. The present invention may be used to produce ethanol from a fermentable material, whether this fermentable material is a material which initially contains fermentable sugars, or whether the fermentable sugars are the result of previous processing steps.

What is claimed is:

1. A method for producing alcohol, which method comprises:
    (a) providing a mixture of a fermentable material and water;
    (b) controlling the temperature of said mixture of fermentable material and water to ferment said fermentable material into alcohol and thereby produce a mixture of alcohol and water;
    (c) supplying thermal energy to said mixture of alcohol and water to distill said alcohol;

(d) providing an internal combustion engine of the type that adds thermal energy to a liquid coolant as said coolant flows through cooling passages of said engine;
(e) providing a liquid coolant;
(f) directing said liquid coolant through said cooling passages, whereby the thermal energy of said coolant is increased;
(g) utilizing thermal energy of exhaust gases of said internal combustion engine to increase the thermal energy of said coolant;
(h) utilizing the thermal energy of said coolant for said supplying step (c); and
(i) loading the mechanical output of said internal combustion engine to increase the thermal energy of said engine.

2. A method as claimed in claim 1 in which said method further comprises adjusting said load (1i) to provide thermal energy from said engine that is sufficient for said supplying step (1c).

3. A method as claimed in claim 1 in which:
(a) said controlling step (1b) comprises supplying thermal energy to said mixture; and
(b) said method further comprises utilizing said thermal energy of said coolant for said step of supplying thermal energy to said mixture (a).

4. A method as claimed in claim 1 in which said method further comprises:
(a) condensing said distilled alcohol;
(b) said condensing step (a) comprises supplying water to a condensor;
(c) said step of supplying water to said condensor (b) comprises pumping water from an external supply; and
(d) said loading step (1i) comprises utilizing said engine for said pumping step (c).

5. A method as claimed in claim 2 in which said loading step (1i) comprises electrically loading.

6. A method as claimed in claim 5 in which said electrical loading step comprises:
(a) providing a generator;
(b) utilizing the mechanical output of said engine to power said generator;
(c) charging a battery; and
(d) said adjusting of said load (19) comprises adjusting the electrical output of said generator.

7. A method as claimed in claim 5 in which said electrical loading step comprises:
(a) providing a generator;
(b) utilizing the mechanical output of said engine to power said generator;
(c) connecting the electrical output of said generator to a watt-hour meter;
(d) connecting the watt-hour meter to the power line of a utility company; and
(e) said adjusting of said load (19) comprises adjusting the electrical output of said generator.

8. A method as claimed in claim 2 in which said loading step (1i) comprises:
(a) providing a compressor; and
(b) compressing a gas with said compressor.

9. A method as claimed in clalim 8 in which said loading step (1i) further comprises compressing a refrigerant gas with said compressor.

10. A method as claimed in claim 1 in which said method further comprises:
(a) producing a wet bulk resisdue that has food value;
(b) applying heat to said wet bulk residue to dry said residue into a meal that is substantially anhydrous; and
(c) utilizing said thermal energy of said coolant for said applying step (b).

11. A method as claimed in claim 1 in which said method further comprises:
(a) producing a wet bulk residue that has food value;
(b) providing a dryer of the rotating drum type;
(c) utilizing mechanical power from said engine to rotate said drum; and
(d) applying thermal energy from said coolant to said wet bulk residue.

12. A method as claimed in claim 1 in which the first said utilizing step (1g) comprises utilizing the heat of condensation of water vapor in said exhaust gases.

13. A method as claimed in claim 1 in which said internal combustion engine is fueled with an alcohol fuel that includes at least five percent water; and
the first said utilizing step (1g) comprises utilizing the heat of condensation of water vapor in said exhaust gases.

14. A method for producing ethanol from tubers, which method comprises:
(a) providing an internal combustion engine of the type that adds thermal energy to a liquid coolant as said coolant flow through cooling passages of said engine;
(b) providing a liquid coolant;
(c) directing said liquid coolant through said cooling passages, whereby the thermal energy of said coolant is increased;
(d) utilizing thermal energy of exhaust gases of said internal combustion engine to increase the thermal energy of said coolant;
(e) separating a mixture of fermentable material and water from the pulp of said tubers;
(f) controlling the thermal energy to said mixture of fermentable material and water to ferment said fermentable material into enthanol and thereby produce a mixture of ethanol and water;
(g) supplying thermal energy to said mixture of ethanol and water to distill said ethanol;
(h) utilizing thermal energy of said coolant for said supplying step (g) and
(i) loading the mechanical output of said engine, whereby said thermal energy produced by said engine is increased.

15. A method as claimed in claim 14 in which said method further comprises adjusting said load (14i) to provide thermal energy from said engine that is sufficient for said supplying step (14g).

16. A method as claimed in claim 14 in which:
(a) said separating step (14e) comprises macerating said tubers; and
(b) said loading step (14i) comprises providing a macerator and connecting said macerator to the mechanical output of said engine.

17. A method as claimed in claim 16 in which:
(a) said separating step (14e) further comprises pressing; and
(b) said loading step (14i) further comprises said pressing step (a).

18. A method as clamed in claim 14 in which method further comprises:
(a) providing a dryer of the rotating drum type;
(b) placing said pulp into said dryer;
(c) rotating said drum; and (d) supplying heat to said dryer.

19. A method as claimed in claim 18 in which:
   (a) said loading step (14i) comprises said step of rotating said drum (18c); and
   (b) said step of supplying heat to said dryer (18d) comprises utilizing said thermal energy of said coolant.

20. A method as claimed in claim 19 in which said method further comprises adjusting said load (14i) to provide thermal energy from said engine that is sufficient for both of said supplying steps (14g & 18d).

21. A method as claimed in claim 14 in which:
   (a) said controlling step (14f) comprises supplying thermal energy to said mixture; and
   (b) said method further comprises utilizing said thermal energy of said coolant for said step of supplying thermal energy to said mixture (a).

22. A method for supplying thermal energy to a step in a process for producing alcohol, which method comprises:
   (a) providing an internal combustion engine of the type that includes a mechanical output, that increases the thermal energy of a fluid flowing through cooling passages thereof, and that rejects thermal energy in the exhaust gases thereof;
   (b) providing a fluid;
   (c) transferring thermal energy from said exhaust gases to said fluid, whereby the thermal energy of said fluid is increased;
   (d) directing said fluid through said cooling passages of said engine, whereby the thermal energy of said fluid is increased;
   (e) supplying thermal energy from said fluid to said step in said process; and
   (f) loading the mechanical output of said engine, whereby the total increase in thermal energy of said transferring (c) and directing (d) steps is increased.

23. A method as claimed in claim 22 in which said method comprises adjusting said load (22f) to provide a total increase in thermal energy from said transferring (22c) and directing (22d) steps that is substantially sufficient for said supplying step (22e).

24. A method for supplying substantially the total required thermal energy to a plurality of thermal energy requirements that includes supplying thermal energy to a step in a process for producing alcohol, which method comprises:
   (a) providing an internal combustion engine of the type that includes a mechanical output, that increases the thermal energy of a fluid flowing through cooling passages thereof, and that rejects thermal energy in the exhaust gases thereof;
   (b) providing a fluid;
   (c) providing a heat exchanger;
   (d) directing said exhaust gases from said engine through said heat exchanger;
   (e) increasing the thermal energy of said fluid by directing said fluid through said heat exchanger;
   (f) increasing the thermal energy of said fluid by directing said fluid through said cooling passages of said engine;
   (g) supplying substantially said total required thermal energy from said fluid to said plurality of thermal energy requirements; and
   (h) loading the mechanical output of said engine, whereby the total increase in thermal energy of said increasing steps (e & f) is increased.

25. A method as claimed in claim 24 in which said method comprises adjusting said load (24h) to provide a total increase in thermal energy of said fluid from said increasing steps (24e & 24f) that is substantially sufficient for said supplying step (24g).

26. A method as claimed in clailm 25 in which said loading (24h) and adjusting (25) steps comprise:
   (a) providing a generator;
   (b) utilizing the mechanical output of said engine to drive said generator;
   (c) connecting the electrical output of said generator to an electrical load; and
   (d) adjusting the electrical output of said generator.

27. A method as claimed in claim 25 in which said loading (24h) and adjusting (25) steps comprise:
   (a) providing a generator;
   (b) utilizing the mechanical output of said engine to drive said generator;
   (c) connecting the electrical output of said generator to a watt-hour meter;
   (d) connecting said watt-hour meter to the power line of a utility company; and
   (e) adjusting the electrical output of said generator.

28. A method as claimed in claim 24 in which said method comprises adjusting said load (24h) to provide a total increase in thermal energy of said fluid from said increasing steps (24e & 24f) that is substantially equal to said supplying step (24g).

29. A method as claimed in claim 24 in which said alcohol producing process comprises producing a wet residue that has food value; and
   said plurality of said thermal energy requirements comprises supplying thermal energy to said wet residue.

30. A method as claimed in claim 29 in which said method comprises adjusting said load (24h) to provide a total increase in thermal energy of said fluid from said increasing steps (24e & 24f) that is substantially sufficient for said supplying step (24g & 29).

31. A method as claimed in claim 29 in which said method comprises adjusting said load (24h) to provide a total increase in thermal energy of said fluid from said increasing steps (24e & 24f) that is substantially equal to the thermal energy of said supplying steps (24g & 29).

32. A method for supplying substantially the total required thermal energy to a plurality of thermal energy requirements that include a step in a process for producing alcohol, which method comprises:
   (a) providing a source of thermal energy;
   (b) supplying a portion of said total required thermal energy from said source of thermal energy;
   (c) providing an internal combustion engine of the type that includes a mechanical output, that increases the thermal energy of a fluid flowing through cooling passages thereof, and that rejects thermal energy in the exhaust gases thereof;
   (d) providing a fluid;
   (e) providing a heat exchanger;
   (f) directing said exhaust gases from said engine through said heat exchanger;
   (g) increasing the thermal energy of said fluid by directing said fluid through said heat exchanger;
   (h) increasing the thermal energy of said fluid by directing said fluid through said cooling passages of said engine;
   (i) supplying substantially the remainder of said total required thermal energy from said fluid; and (j) loading the mechanical output of said engine, whereby the total increase in thermal energy of said increasing steps (g & h) is increased.

33. A method as claimed in claim 32 in which said method comprises adjusting said load (32i) to provide a total increase in thermal energy of said fluid from said increasing steps (32g & 32h) that is substantially sufficient for the second said supplying step (32i).

34. A method as claimed in claim 33 in which said loading (32i) and adjusting (33) steps comprise:
(a) providing a generator;
(b) utilizing the mechanical output of said engine to drive said generator;
(c) connecting the electrical output of said generator to an electrical load; and
(d) adjusting the electrical output of said generator.

35. A method as claimed in claim 33 in which said loading (32j) and adjusting (33) steps comprise:
(a) providing a generator;
(b) utilizing the mechanical output of said engine to drive said generator;
(c) connecting the electrical output of said generator to a watt-hour meter; and
(d) connecting said watt-hour meter to the power line of a utility company; and
(e) adjusting the electrical output of said generator.

36. A method as claimed in claim 32 in which said method comprises adjusting said load (32j) to provide a total increase in thermal energy of said fluid from said increasing steps (32g & 32h) that is substantially equal to the thermal energy of the second said supplying step (32i).

37. A method as claimed in claim 32 in which said alcohol producing process comprises producing a wet residue that has food value; and
said plurality of said thermal energy requirements comprises supplying thermal energy to said wet residue.

38. A method as claimed in claim 37 in which said method comprises adjusting said load (32j) to provide a total increase in thermal energy of said fluid from said increasing steps (32g & 32h) that is substantially sufficient for the second said supplying step (32i).

39. A method as claimed in claim 37 in which said method comprises adjusting said load (32j) to provide a total increase in thermal energy of said fluid from said increasing steps (32g & 32h) that is substantially equal to the thermal energy of the second said supplying step (32i).

* * * * *